US009050208B2

(12) United States Patent
Locke et al.

(10) Patent No.: US 9,050,208 B2
(45) Date of Patent: Jun. 9, 2015

(54) SYSTEMS AND METHODS FOR DELIVERING FLUID TO A WOUND THERAPY DRESSING

(75) Inventors: Christopher Locke, Bournemouth (GB); Kevin Bendele, Adkins, TX (US); James Luckemeyer, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 39 days.

(21) Appl. No.: 13/477,659

(22) Filed: May 22, 2012

(65) Prior Publication Data

US 2012/0302976 A1    Nov. 29, 2012

Related U.S. Application Data

(60) Provisional application No. 61/490,880, filed on May 27, 2011.

(51) Int. Cl.
  *A61M 1/00*  (2006.01)
  *A61F 13/00*  (2006.01)

(52) U.S. Cl.
  CPC ........ *A61F 13/00068* (2013.01); *A61M 1/0023* (2013.01); *A61M 1/0031* (2013.01); *A61M 1/0037* (2013.01); *A61M 1/0058* (2013.01); *A61M 1/0084* (2013.01); *A61M 1/0088* (2013.01); *A61M 2205/3344* (2013.01)

(58) Field of Classification Search
  CPC ... A61M 1/00; A61M 1/0023; A61M 1/0031; A61M 1/0037; A61M 1/0058; A61M 1/0062; A61M 27/00; A61F 13/00068
  USPC .................................. 604/289, 317, 318, 543
  See application file for complete search history.

(56) References Cited

U.S. PATENT DOCUMENTS

| 2007/0118096 A1* | 5/2007 | Smith et al. ................... 604/541 |
| 2007/0179460 A1 | 8/2007 | Adahan ......................... 604/319 |
| 2008/0294127 A1 | 11/2008 | Blott et al. .................... 604/305 |
| 2009/0275884 A1 | 11/2009 | McNulty et al. ............... 604/35 |
| 2009/0306609 A1* | 12/2009 | Blott et al. .................... 604/305 |
| 2010/0018370 A1* | 1/2010 | Tumey et al. ................... 83/100 |
| 2011/0015587 A1 | 1/2011 | Tumey et al. ................. 604/290 |
| 2011/0034861 A1* | 2/2011 | Schaefer ........................ 604/23 |
| 2011/0054283 A1* | 3/2011 | Shuler ........................... 600/364 |

FOREIGN PATENT DOCUMENTS

WO    WO 2008/130689    10/2008

OTHER PUBLICATIONS

Craig ("Fluid Systems" Rennselear Polytechnic Institute, retrieved by the USPTO from http://multimechatronics.com/images/uploads/mech_n/Fluid_Systems.pdf on Dec. 25, 2014, available as of Aug. 23, 2014 according to web.archive.org).*
Bedarada, et al. "Polymeric microcapsules with light responsive properties for encapsulation and release". Advances in Colloid and Interface Science. vol. 158, Issue 1-2, Jul. 12, 2010, pp. 2-14.
International Search Report and Written Opinion issued for PCT Patent Application No. PCT/US2012/038945, Dated Jul. 25, 2012.
International Search Report and Written Opinion issued for PCT Patent Application No. PCT/US2012/034429, Dated Jul. 4, 2012.
U.S. Appl. No. 13/452,014, filed Apr. 20, 2012, Coulthard, et al.
U.S. Appl. No. 13/477,741, filed May 22, 2012, Locke, et al.
Kooiman, et al. "Oil-filled polymer microcapsules for ultrasound-mediated delivery of lipophilic drugs". Journal of Controlled Release 133 (2009)2.—ISSN 0168-3659—p. 109-118.
Peteu, et al. "Responsive Polymers for Crop Protection." Polymers, 2010, 2, 229-251; doi:10.3390/polym2030229.

* cited by examiner

*Primary Examiner* — Philip R Wiest
*Assistant Examiner* — Benjamin Klein

(57) ABSTRACT

Systems and methods for delivery of fluid to a wound therapy dressing. In exemplary embodiments, a pressure sensor measures the pressure at the wound therapy dressing and restricts fluid flow to the wound therapy dressing when a predetermined pressure is achieved.

20 Claims, 6 Drawing Sheets

SYSTEMS AND METHODS FOR DELIVERING FLUID TO A WOUND THERAPY DRESSING

CROSS-REFERENCE TO RELATED APPLICATIONS

This application claims priority to U.S. Provisional Patent Application Ser. No. 61/490,880, filed May 27, 2011, the entire contents of which are incorporated herein by reference.

BACKGROUND OF THE INVENTION

1. Field of the Invention

Embodiments of the invention relate to fluid (e.g., liquid) delivery to a wound therapy dressing and more particularly relate to systems and methods for automated fluid delivery to a negative pressure wound therapy dressing.

2. Description of the Related Art

Existing fluid delivery systems for wound therapy dressings are typically based on infusion systems. It is worth noting that with drug delivery systems, the user is responsible for determining the dosage of the fluids and would not generally use an automated system to determine the desired volume of liquid that should be delivered.

However, if one considers the art with respect to fluid delivery for wound dressings, such an approach may not be appropriate. For example, wound dressing fluid delivery systems are not delivering intravenous drugs. Furthermore, wounds are not uniform and indeed will change volume as the therapy progresses. Consequently, using techniques employed in other areas to prescribe a dose volume may result in under- or over-delivery of fluids with the commensurate problems. In existing delivery systems, fluid pressure may be monitored to determine if there is a line blockage, but it is typically not monitored to determine the pressure of the fluid at the site of delivery.

The referenced shortcomings are not intended to be exhaustive, but rather are among many that tend to impair the effectiveness of previously known techniques in fluid delivery to wound dressings; however, those mentioned here are sufficient to demonstrate that the methodologies appearing in the art have not been satisfactory and that a significant need exists for the techniques described and claimed in this disclosure. Instillation of fluid as an adjunct to negative pressure wound therapy (NPWT) is currently accomplished by asking the user to specify an instillation time (gravity feed systems) or instillation volume (active pumping systems).

Because it is difficult to judge the volume of a dressed wound, either approach can be problematic and time-consuming to arrive at the desired fill volume. A "Fill Assist" approach has also been used, which requires the user to stop metered fluid flow based on visual observation of the wound filling; whereafter, the automated system dispenses the same volume in subsequent instillation cycles.

However, even this simplified approach requires that the user be attentive to stopping the flow, and can easily lead to over-filling the wound, waste of NPWT collection canister volume, and potentially instillation fluid leakage at the dressing. It is therefore desirable that automated systems and methods be developed to allow the user to determine when the wound dressing has received the proper volume of liquid for instillation.

SUMMARY OF THE INVENTION

From the foregoing discussion, it should be apparent that a need exists for a system and method for improved delivery of fluid to a wound therapy dressing.

The method in the disclosed embodiments substantially includes the steps necessary to carry out the functions presented above with respect to the operation of the described system.

Exemplary embodiments of the present disclosure can provide automated delivery of fluid to a wound therapy dressing. Such automation not only frees a caregiver from having to be attentive to the device rather than the patient, but addresses a perceived problem in that the caregiver may have difficulty making a judgment about when the dressing is appropriately filled.

Exemplary embodiments can provide for increased efficiency in both caregiver's time and reduced waste of instillation fluids. For example, exemplary embodiments can reduce the likelihood of accidental overfilling of the dressing caused by a distracted or non-attentive user or caregiver. Such overfilling can require a time-consuming cycling of the system in order to repeat the fluid delivery feature or cause other operational issues. Further, there is no requirement for the caregiver to estimate wound volume or provide other input to the automated fill system.

Exemplary embodiments of this disclosure provide an automated fluid delivery system, improving the caregiver's ability to determine the correct fill level which in turn ensures that the pneumatic performance is not compromised by an overfill condition.

Exemplary embodiments of the present disclosure are configured for delivering fluid to a volume space, which have (prior to instillation) been evacuated to a known pressure and verified to not have leaks. Exemplary embodiments have the advantage of using the equalization of pressure which occurs as a fluid fills the dressing volume to provide an indicator of the correct fill level.

Certain embodiments include a system for delivering fluid to a negative pressure wound therapy dressing. In specific embodiments, the system comprises: a wound dressing; a negative pressure source coupled to the wound dressing; a fluid flow device in fluid communication with the wound dressing; a control device configured to control a fluid flow from the fluid flow device; and a pressure sensor coupled to the wound dressing and to the control device. In particular embodiments, the pressure sensor is configured to send a control signal to the control device and control fluid flow from the fluid flow device when pressure sensor detects a predetermined pressure at the wound dressing. Certain embodiments comprise a visual or audible indicator when the pressure sensor detects the predetermined pressure at the wound dressing. In particular embodiments, the fluid flow device can be a pump, including for example, a peristaltic pump or a centrifugal pump. In certain embodiments the fluid flow device can be a valve.

In specific embodiments, the control device is a control switch configured to turn the pump on or off. In particular embodiments, the control device is an actuator configured to change the position of the valve. In certain embodiments, the fluid flow device is a solenoid-actuated pinch valve. Particular embodiments may further comprise a reservoir coupled to the negative pressure source and in fluid communication with the fluid flow device. In specific embodiment, a fluid can flow from the reservoir to the wound dressing via a gravity feed system.

Particular embodiments may also comprise a check valve between the wound dressing and the reservoir, where the check valve is configured to restrict fluid flow to the reservoir when the reservoir is not at a negative pressure. In certain embodiments, the control device comprises a control switch configured to stop operation of the fluid flow device when the pressure sensor detects a predetermined pressure at the wound dressing. In specific embodiments, the control device comprises a solenoid valve configured to close when the pressure sensor detects a predetermined pressure at the wound dressing. In particular embodiments, the predetermined pressure is between approximately −1.0 mm Hg and 1.0 mm Hg, and in specific embodiments approximately 0.0 mm Hg.

Certain embodiments comprise a method for delivering fluid to a wound therapy dressing. In particular embodiments, the method comprises: creating a negative pressure on a wound therapy dressing; delivering fluid to the wound therapy dressing; monitoring pressure at the wound therapy dressing via a pressure sensor; and restricting fluid delivery when the pressure reaches a predetermined value. In specific embodiments, restricting the fluid delivery comprises activating a control switch to cut off a supply of energy to a pump. In particular embodiments, restricting fluid delivery comprises closing a valve between a fluid flow device and the wound therapy dressing. In certain embodiments, the valve can be a solenoid valve.

Specific embodiments further comprise deactivating the negative pressure source prior to delivering fluid to the wound therapy dressing. Certain embodiments further comprise providing fluid flow to the wound therapy dressing via a gravity feed system. Particular embodiments further comprise providing a reservoir between the negative pressure source and the wound therapy dressing. Certain embodiments can also comprise providing a check valve between the negative pressure source and the wound therapy dressing, where the check valve is configured to restrict flow from the negative pressure source to the wound therapy dressing. Specific embodiments can also comprise venting the reservoir to atmosphere after de-activating the negative pressure source and prior to activating the pump to deliver fluid to the wound therapy dressing. In particular embodiments, the predetermined pressure is between approximately −1.0 mm Hg and 1.0 mm Hg, and in specific embodiments approximately 0.0 mm Hg.

Other features and associated advantages will become apparent with reference to the following detailed description of specific embodiments in connection with the accompanying drawings.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "negative pressure" refers to an absolute pressure that is lower than the absolute atmospheric pressure at the location of use of the device. A stated level of negative pressure in a region is therefore a relative measure between the absolute atmospheric pressure and the absolute pressure in the region. A statement that the negative pressure is increasing means the pressure in the region is moving towards atmospheric pressure (i.e. the absolute pressure is increasing). Where numeric values are used, a negative sign is placed in front of the numeric pressure value to indicate the value is a negative pressure relative to atmospheric pressure.

BRIEF DESCRIPTION OF THE DRAWINGS

The following drawings form part of the present specification and are included to further demonstrate certain aspects of exemplary embodiments of the present invention.

DETAILED DESCRIPTION OF EXEMPLARY EMBODIMENTS

Various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

In the following description, numerous specific details are provided, such as examples of material selections, dimensions, etc., to provide a thorough understanding of the present embodiments. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
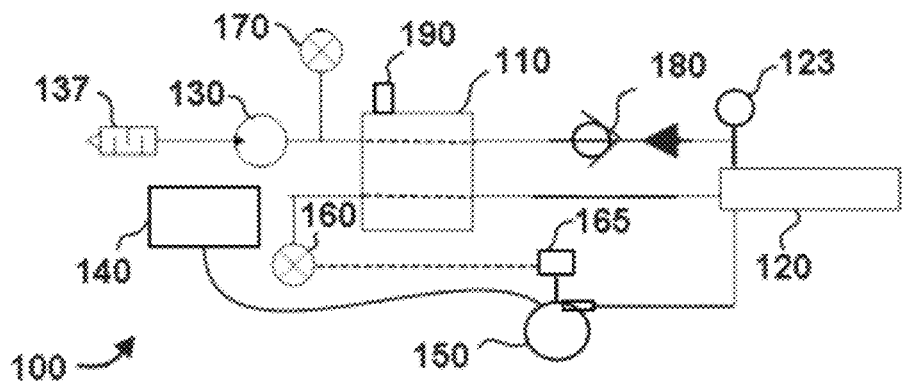
FIG. 1 is a schematic block diagram illustrating one embodiment of a system for delivering fluid to a wound therapy dressing in a first mode of operation.
Figure 2:
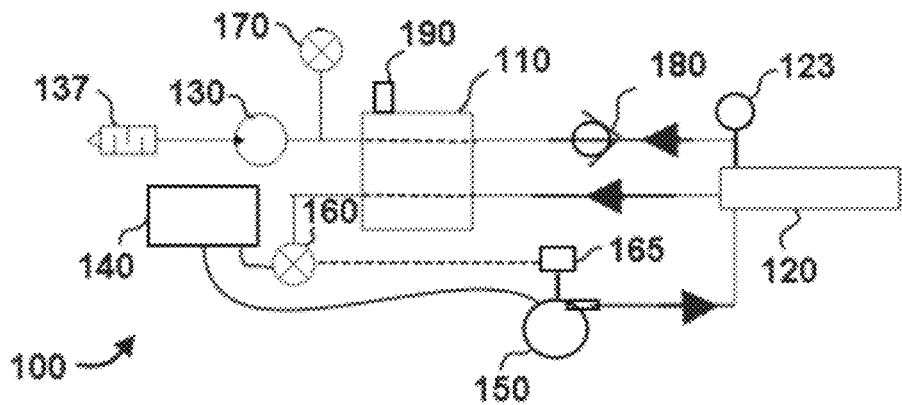
FIG. 2 is a schematic block diagram of the embodiment of FIG. 1 in a second mode of operation.
Figure 3:
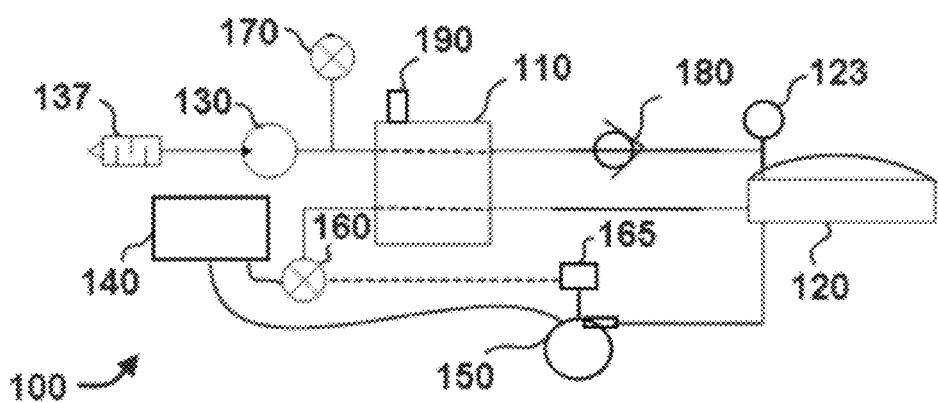
FIG. 3 is a schematic block diagram of the embodiment of FIG. 1 in a third mode of operation.

FIGS. 1-3 illustrate one embodiment of a system 100 for providing fluid delivery to a negative pressure wound therapy system. In the exemplary embodiment shown, system 100 includes a reservoir 110, a wound dressing 120, and a negative pressure source 130 coupled to reservoir 110 and wound dressing 120. In this embodiment, system 100 further comprises a fluid flow device 150 (e.g. a pump or valve, as discussed below) in fluid communication with a fluid supply reservoir 140 and wound dressing 120.

Certain embodiments may utilize a gravity fluid flow from fluid supply reservoir 140 to wound dressing 120 without utilizing a pumping device for fluid flow device 150. In such embodiments, fluid flow device 150 may be a valve (e.g., a solenoid-actuated pinch valve) configured to control the flow of fluid between fluid supply reservoir 140 and wound dressing 120. In still other embodiments, negative pressure source 130 may draw fluid into wound dressing 120 from fluid supply reservoir 140, without the aid of gravity feed or a pumping action from fluid flow device 150.

In particular exemplary embodiments, negative pressure source 130 may comprise a diaphragm vacuum pump. In certain embodiments, system 100 may also comprise a filter or muffler 137 coupled to negative pressure source 130 to reduce the operating noise of negative pressure source 130 and/or filter air exiting negative pressure source 130.

In certain exemplary embodiments, fluid flow device 150 may comprise a pump, e.g., a peristaltic, centrifugal or other suitable pump. In other exemplary embodiments, fluid flow device may comprise a gravity feed system instead of (or in conjunction with) a pump to deliver fluid to wound dressing 120. In such embodiments, a valve between the gravity feed system and wound dressing 120 can be used to restrict the fluid flow to wound dressing 120 when the predetermined pressure is reached, as explained more fully below.

In the disclosed embodiment, system 100 also comprises a vent 190 on reservoir 110, and a check valve 180 configured to allow flow in the direction from wound dressing 120 towards negative pressure source 130, and restrict fluid flow in the reverse direction. The exemplary embodiment shown in FIGS. 1-3 also comprises a pressure sensor 160 coupled to wound dressing 120, as well as a pressure sensor 170 coupled to negative pressure source 130 and wound dressing 120.

FIGS. 1-3 illustrate three modes of operation of system 100. In FIG. 1, negative pressure source 130 is activated to create a negative pressure on wound dressing 120, while fluid flow device 150 is not activated. In FIG. 2, negative pressure source 130 is not activated, but fluid flow device 150 is activated to provide a fluid flow to wound dressing 120. In FIG. 3, both negative pressure source 130 and fluid flow device 150 are not activated.

During initial operation of system 100 shown in FIG. 1, negative pressure source 130 is activated to create a negative pressure on reservoir 110 and wound dressing 120. The pressure at negative pressure source 130 and reservoir 110 and wound dressing 120 can be monitored via pressure sensor 170, as well as pressure sensor 160 (assuming normal operation without blockages in the conduit coupling the components). When the desired level of negative pressure (e.g., −125 mm Hg) is achieved, negative pressure source 130 can be deactivated and vent 190 can be opened to vent reservoir 110 to atmosphere. In certain embodiments, check valve 180 maintains the negative pressure on wound dressing 120, which can be monitored via pressure sensor 160. In particular embodiments, check valve 180 may be a duckbill type or ball-check type or flap type valve.

Fluid flow device 150 can then be activated to begin fluid delivery to wound dressing 120. In particular embodiments, fluid flow device 150 may be configured to flow approximately 100 ml/minute. As fluid is pumped from fluid flow device 150 to wound dressing 120, the pressure at wound dressing 120 (which can be monitored via pressure sensor 160) will increase. When wound dressing 120 reaches a predetermined pressure, pressure sensor 160 (which may be used to sense both positive and negative pressures) can send a control signal to control device 165 (e.g. a control switch or actuator) to restrict fluid flow from fluid flow device 150 to wound dressing 120. The increase in pressure of wound dressing 120 can be used as an indication that fluid from fluid flow device 150 has sufficiently filled wound dressing 120. By monitoring the pressure of wound dressing 120 with pressure sensor 160, system 100 can reduce the likelihood that wound dressing 120 will be overfilled. This can reduce waste of fluid and leakage of wound dressing associated with overfilling. It is understood that interface circuitry (not shown) may be utilized to generate a sufficiently strong control signal and to implement the control logic.

As previously mentioned, in certain embodiments, fluid flow device 150 may be a valve (e.g., a solenoid-actuated pinch valve) that restricts fluid flow from fluid supply reservoir 140 or a pump that is activated to provide fluid flow. The operation of fluid flow device 150 (e.g., the position of a valve or the activation/deactivation of a pump) may be automatically altered when a predetermined pressure is reached at wound dressing 120. In exemplary embodiments, the predetermined pressure of wound dressing 120 at which the operation of fluid flow device 150 is altered may be approximately 1.0 mm Hg (gauge pressure as measured by pressure indicator 160). In specific embodiments the predetermined pressure may be −10 and 10 mm Hg, including −10, −9, −8, −7, −6, −5, −4, −3, −2, −1, 0, 1, 2, 3, 4, 5, 6, 7, 8, 9 or 10 mm Hg, or any values between.

In other embodiments a user may monitor pressure sensor 160 and manually control operation of fluid flow device 150 when wound dressing 120 reaches the predetermined pressure. For example, a user may deactivate fluid flow device 150 by manipulating a control switch or restrict fluid flow from fluid flow device 150 by closing a valve.

When wound dressing 120 is sufficiently filled with fluid, the user may continue with the desired fluid instillation and vacuum therapy treatments. Exemplary embodiments can be used for each instillation cycle, which may offer advantages for wound dressings on articulated joints (e.g., knee) where the wound or dressing volume could be influenced by the patient's body position. In certain embodiments utilizing a foam dressing, the dressing volume can change over time in part due to compression-set of the foam. For example, the volume of the foam may be reduced over time as the foam is subjected to pressure. This change in volume occupied by the foam can affect the volume of fluid needed to fill wound dressing 120. Such volume changes can be accommodated by exemplary embodiments, which utilize pressure readings to indicate when the wound dressing has received a sufficient volume of liquid.

It is understood that the features shown FIGS. 1-3 and described in the accompanying discussion of the figures are merely one exemplary embodiment of the present disclosure. Other embodiments, for example, may utilize absorption layers in the wound dressing instead of, or in addition to, a reservoir.

Figure 4:
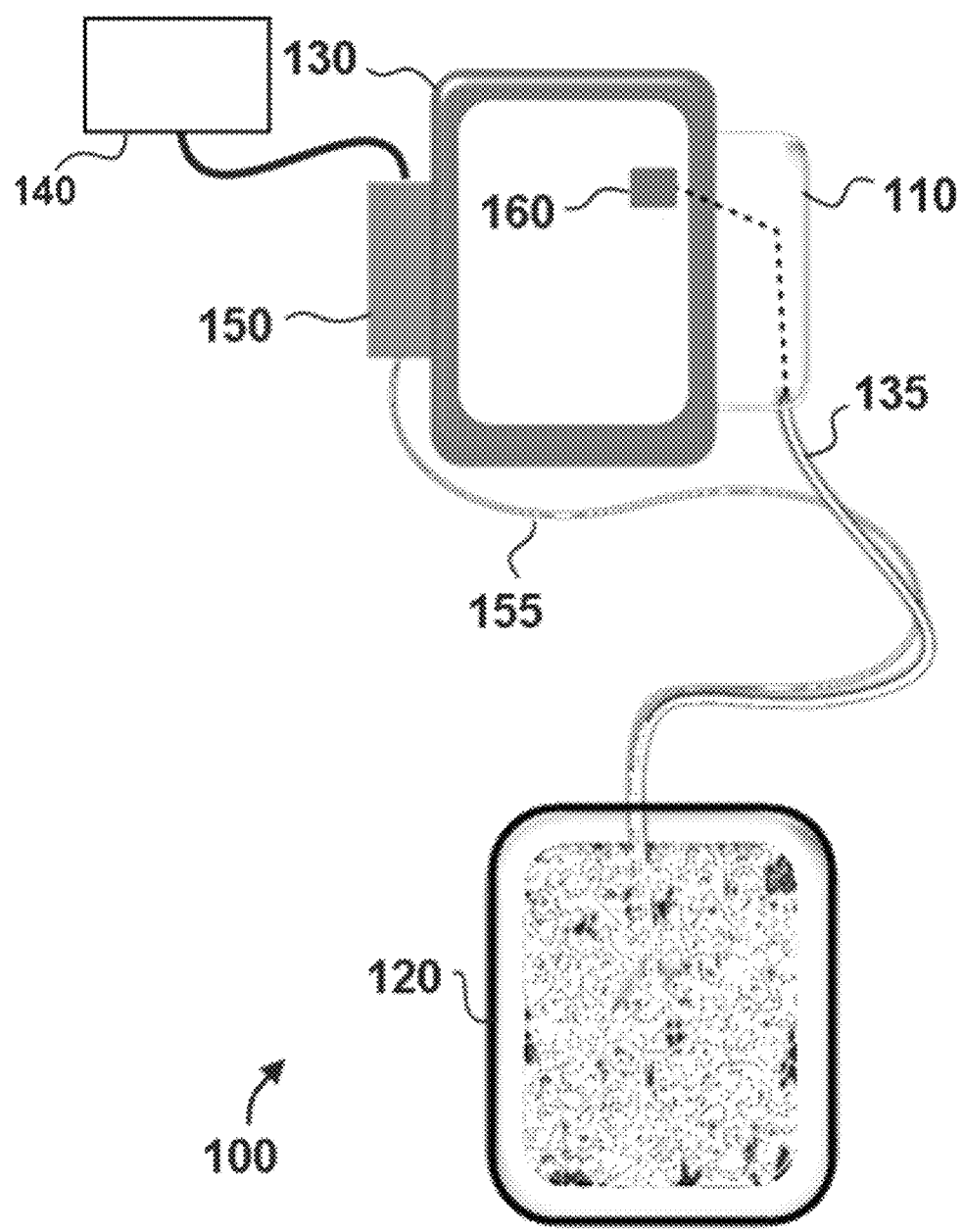
FIG. 4 is an orthogonal view illustrating the embodiment of FIG. 1 for delivering fluid to a wound therapy dressing in a first mode of operation.
Figure 5:
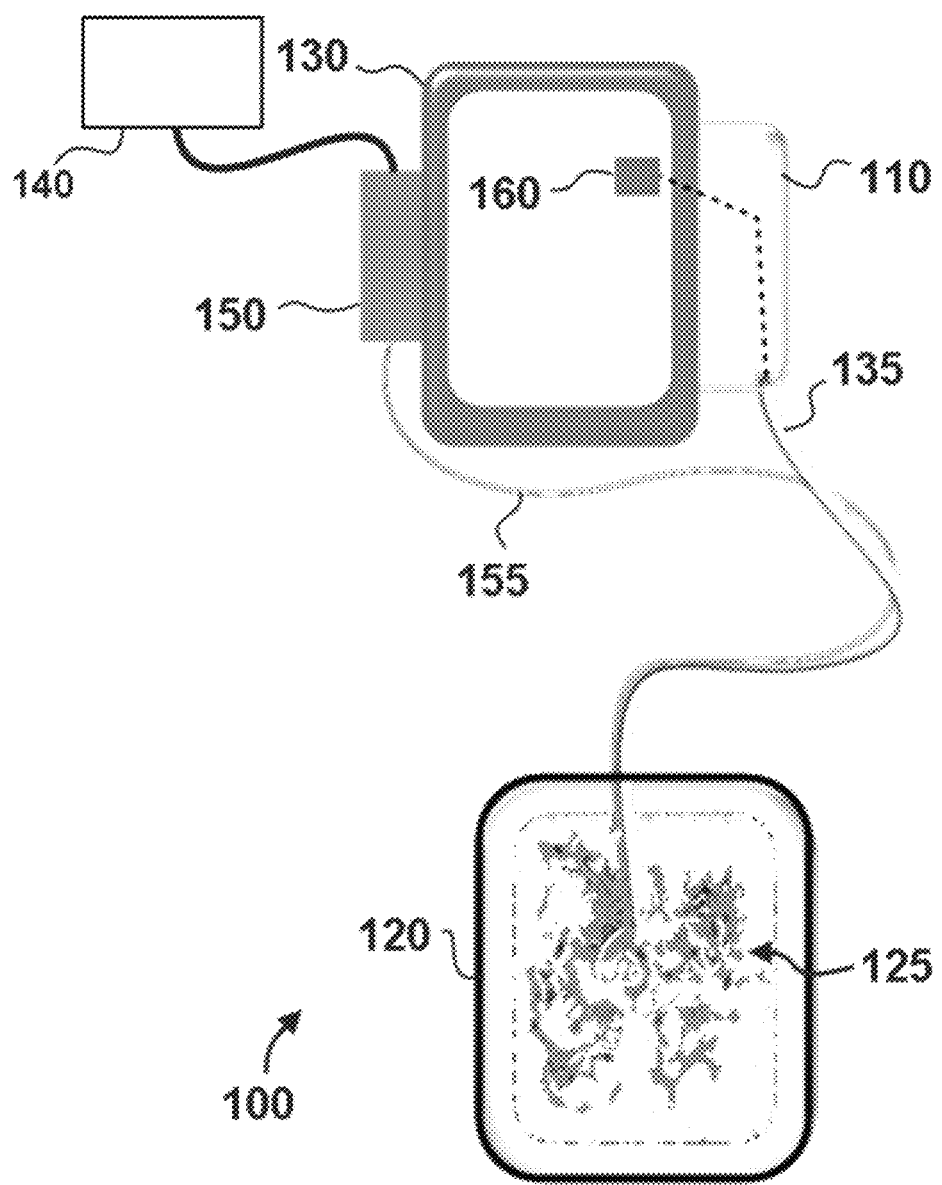
FIG. 5 is an orthogonal view illustrating the embodiment of FIG. 4 in a second mode of operation.
Figure 6:
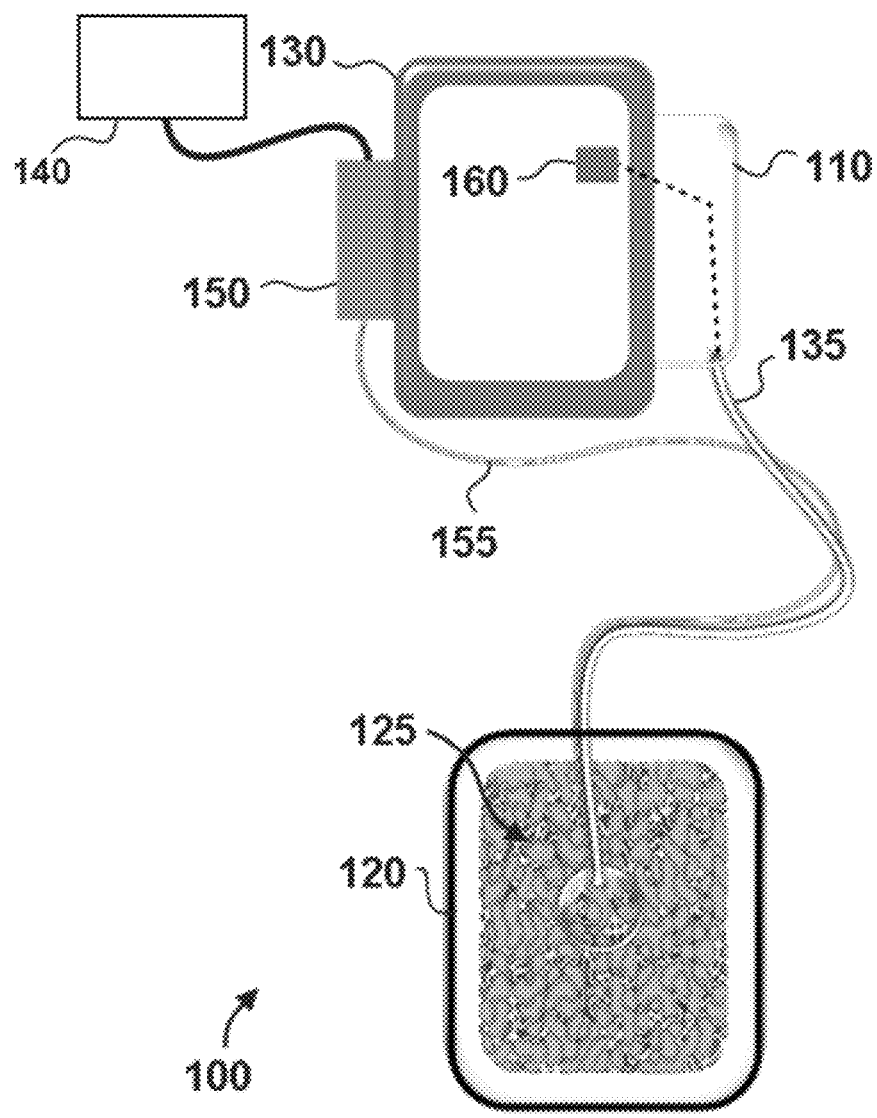
FIG. 6 is an orthogonal view illustrating the embodiment of FIG. 4 in a second mode of operation.

Referring now to FIGS. 4-6, orthogonal views of previously-described system 100 are shown in the three modes of operation illustrated in FIGS. 1-3. In FIG. 4, negative pressure source 130 is activated to create a negative pressure on reservoir 110 and wound dressing 120 (via conduit 135). In this stage of operation, there is no fluid in wound dressing 120.

As shown in FIG. 5, negative pressure source 130 is deactivated, and fluid flow device 150 is activated to begin fluid flow to wound dressing 120. As shown in FIG. 5, fluid 125 from fluid flow device 150 has begun entering wound dressing 120, via conduit 155. As fluid 125 enters wound dressing 120, the pressure measured by pressure sensor 160 increases.

Referring now to FIG. 6, a sufficient volume of fluid 125 has entered wound dressing 120 to increase the pressure to the predetermined pressure, indicating that the desired volume of fluid 125 is located in wound dressing 120. At this stage of operation, pressure sensor 160 can provide information to a control circuit to restrict the flow of fluid 125 from fluid flow device 150. As explained above, pressure sensor 160 may send a control signal to control the operation of fluid flow device 150. For example, pressure sensor 160 may send a control signal to deactivate fluid flow device 150 if it is configured as a pump. Pressure sensor 160 may also send a control signal to close a valve if fluid flow device 150 is configured as a valve.

In certain embodiments, system 100 may comprise an audible or visual pressure indicator 123 at the dressing or elsewhere in the negative pressure path (e.g., a Prevena™ dressing type available from Kinetic Concepts, Inc., San Antonio, Tex. U.S.A. has a visual indicator that retracts when the dressing is below a pressure setpoint and extends when the dressing is above the pressure setpoint) that the predetermined pressure has been reached and that wound dressing 120 contains a sufficient volume of fluid 125. At this stage, the user may proceed with the desired fluid instillation and vacuum therapy treatments.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 7:
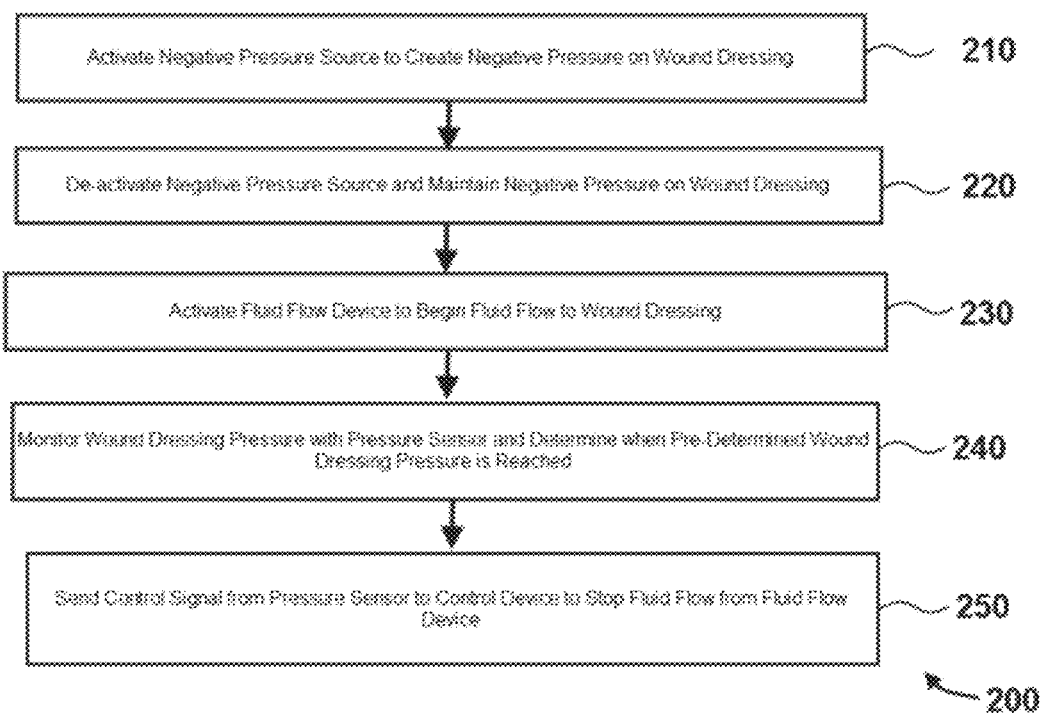
FIG. 7 is a flowchart illustrating a series of steps that can be performed in one embodiment of a method for delivering fluid to a wound therapy dressing.

Referring now to FIG. 7, a method 200 is disclosed comprising a series of steps that may be executed for the operation of an exemplary system according to this disclosure. Certain embodiments may comprise a tangible computer readable medium comprising computer readable code that, when executed by a computer, causes the computer to perform operations comprising the steps disclosed in FIG. 7.

In this exemplary embodiment, step 210 comprises activating the negative pressure source to create negative pressure on the wound dressing. Step 220 comprises de-activating the negative pressure source and maintaining negative pressure on the wound dressing. Step 230 comprises activating the fluid flow device to begin fluid flow to the wound dressing, in this embodiment. Step 240 comprises monitoring the wound dressing pressure with the pressure sensor and determining when the predetermined wound dressing pressure is reached. In this embodiment, step 250 comprises sending a control signal from the pressure sensor to the control device to stop the fluid flow from the fluid flow device.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus, and components may be eliminated or substituted for the components described herein, where the same or similar results would be achieved. All such similar substitutes and modifications apparent to those skilled in the art are deemed to be within the spirit, scope, and concept of the invention as defined by the appended claims.

We claim:

1. A system for delivering fluid to a wound dressing, the system comprising:
    a negative pressure source coupled to the wound dressing;
    a fluid flow device in fluid communication with the wound dressing;
    a reservoir coupled to the negative pressure source and in fluid communication with the wound dressing;
    a vent on the reservoir;
    a valve between the wound dressing and the reservoir;
    a control device configured to control a fluid flow from the fluid flow device; and
    a pressure sensor coupled to the wound dressing and to the control device, the pressure sensor configured to send a control signal to the control device when the pressure sensor detects a predetermined pressure at the wound dressing; and
    wherein the negative-pressure source is configured to evacuate the wound dressing; the vent is configured to open the reservoir to atmosphere; the valve is configured to restrict fluid flow to the reservoir when the reservoir is not at a negative pressure; and the control device is configured to deliver fluid from the fluid flow device to the wound dressing until the pressure sensor sends the control signal.

2. The system of claim 1, further comprising a visual or audible indicator when the pressure sensor detects the predetermined pressure at the wound dressing.

3. The system of claim 1 wherein the fluid flow device is a pump.

4. The system of claim 3 wherein the control device is a control switch configured to turn the pump on or off.

5. The system of claim 1 wherein the fluid flow device is a peristaltic pump.

6. The system of claim 1 wherein the fluid flow device is a centrifugal pump.

7. The system of claim 1 wherein the fluid flow device is a valve.

8. The system of claim 7 wherein the control device is an actuator configured to change the position of the valve.

9. The system of claim 1 wherein the fluid flow device is a solenoid-actuated pinch valve.

10. The system of claim 1 wherein the control device comprises a control switch configured to stop operation of the fluid flow device when the pressure sensor detects a predetermined pressure at the wound dressing.

11. The system of claim 1 wherein the control device comprises a solenoid valve configured to close when the pressure sensor detects a predetermined pressure at the wound dressing.

12. The system of claim 1 wherein the predetermined pressure is approximately 0.0 mm Hg.

13. The system of claim 1 wherein the predetermined pressure is between approximately −1.0 mm Hg and 1.0 mm Hg.

14. A method for delivering fluid to a wound therapy dressing, the method comprising:
- creating a negative pressure on the wound therapy dressing;
- closing a valve to restrict fluid flow from the wound therapy dressing to the negative pressure source;
- delivering fluid to the wound therapy dressing while the valve is closed;
- monitoring pressure at the wound therapy dressing via a pressure sensor while the valve is closed;
- restricting fluid delivery when the pressure reaches a predetermined value, wherein the predetermined value is indicative of a desired volume of the fluid in the wound therapy dressing;
- providing a reservoir between the negative pressure source and the wound therapy dressing;
- deactivating the negative pressure source prior to delivering fluid to the wound therapy dressing; and
- venting the reservoir to atmosphere after de-activating the negative pressure source and prior to delivering fluid to the wound therapy dressing.

15. The method of claim 14 wherein restricting the fluid delivery comprises activating a control switch to cut off a supply of energy to a pump.

16. The method of claim 14 wherein restricting fluid delivery comprises closing a second valve between a fluid flow device and the wound therapy dressing.

17. The method of claim 16 wherein the second valve is a solenoid valve.

18. The method of claim 14 wherein delivering fluid comprises providing fluid flow to the wound therapy dressing via a gravity feed system.

19. The method of claim 14 wherein the predetermined value is approximately 0.0 mm Hg.

20. The method of claim 14 wherein the predetermined value is between approximately −1.0 mm Hg and 1.0 mm Hg.

* * * * *